(12) United States Patent
Sauer

(10) Patent No.: US 11,266,398 B2
(45) Date of Patent: Mar. 8, 2022

(54) AUTOMATED SUTURING ADAPTER, ASSEMBLY, AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc, Victor, NY (US)

( * ) Notice: Subject to any disclaimer, the term of this patent is extended or adjusted under 35 U.S.C. 154(b) by 141 days.

(21) Appl. No.: 16/226,266

(22) Filed: Dec. 19, 2018

(65) Prior Publication Data

US 2019/0183485 A1    Jun. 20, 2019

Related U.S. Application Data

(60) Provisional application No. 62/607,811, filed on Dec. 19, 2017.

(51) Int. Cl.
| | |
|---|---|
| *A61B 17/04* | (2006.01) |
| *A61B 17/062* | (2006.01) |
| *A61F 2/24* | (2006.01) |
| *A61B 17/06* | (2006.01) |
| *A61B 17/00* | (2006.01) |

(52) U.S. Cl.
CPC ...... *A61B 17/0469* (2013.01); *A61B 17/0482* (2013.01); *A61B 17/062* (2013.01); *A61B 17/06166* (2013.01); *A61B 2017/00243* (2013.01); *A61B 2017/0472* (2013.01); *A61B 2017/0496* (2013.01); *A61F 2/2409* (2013.01)

(58) Field of Classification Search
CPC . A61B 17/06; A61B 17/0469; A61B 17/0482; A61B 17/0483; A61B 17/0485; A61B 17/062; A61B 17/06166; A61B 2017/0472; A61B 2017/0496; A61B 2017/00358; A61B 17/32056; A61B 17/0491; A61B 2017/0475
See application file for complete search history.

(56) References Cited

U.S. PATENT DOCUMENTS

| | | | |
|---|---|---|---|
| 2002/0107530 A1* | 8/2002 | Sauer ................ | A61B 17/0469 606/139 |
| 2014/0276979 A1* | 9/2014 | Sauer ................ | A61B 17/0469 606/144 |
| 2015/0289868 A1* | 10/2015 | Sauer ................ | A61B 17/0401 606/144 |
| 2017/0049435 A1* | 2/2017 | Sauer ................ | A61B 17/0469 |
| 2019/0307442 A1* | 10/2019 | Sauer ................ | A61B 17/0483 |

* cited by examiner

*Primary Examiner* — Kathleen S Holwerda
*Assistant Examiner* — Uyen N Vo
(74) *Attorney, Agent, or Firm* — Michael E. Coyne; Christopher B. Miller; David J. Gervasi

(57) ABSTRACT

An automated suturing adapter is disclosed. The automated suturing adapter has a target and a snare loop supported by the target. The automated suturing adapter also has a ferrule and a snare extension between the snare loop and the ferrule. An assembly is also disclosed. The assembly includes a cassette. The cassette has a housing defining a suturing gap. The cassette also has a needle stored in the housing proximal to the suturing gap. The cassette further has a ferrule holder distal to the suturing gap. The assembly also includes a target and a snare loop supported by the target. The assembly further includes a ferrule held in the ferrule holder and a snare extension between the snare loop and the ferrule.

4 Claims, 7 Drawing Sheets

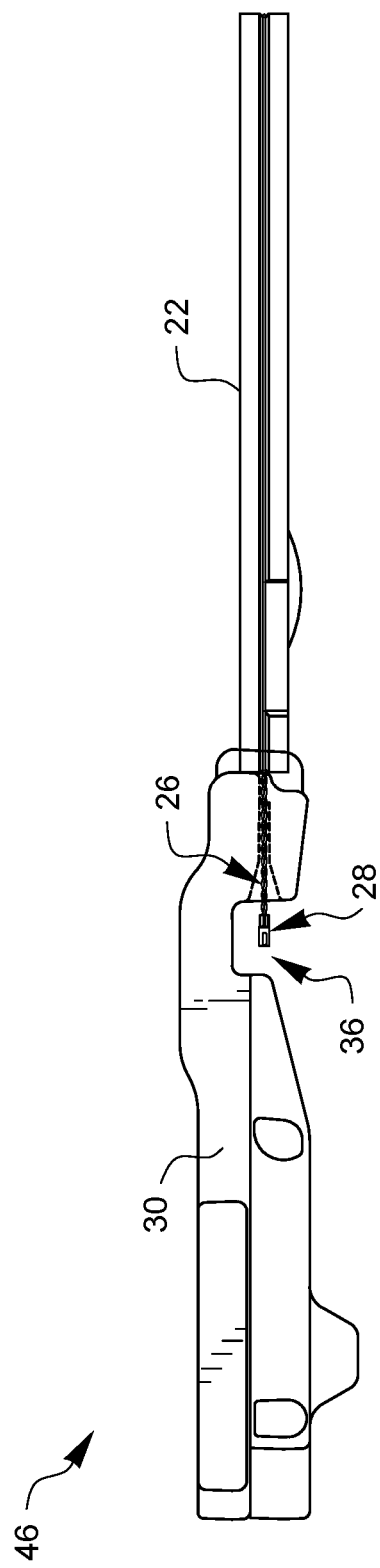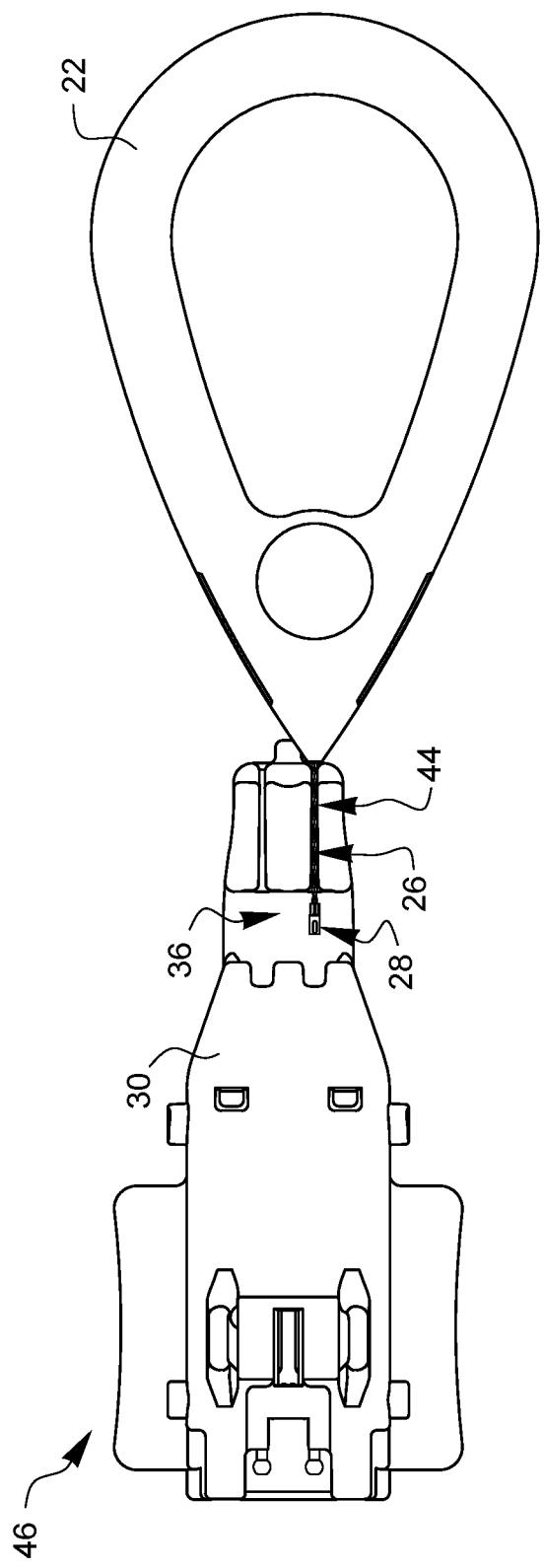

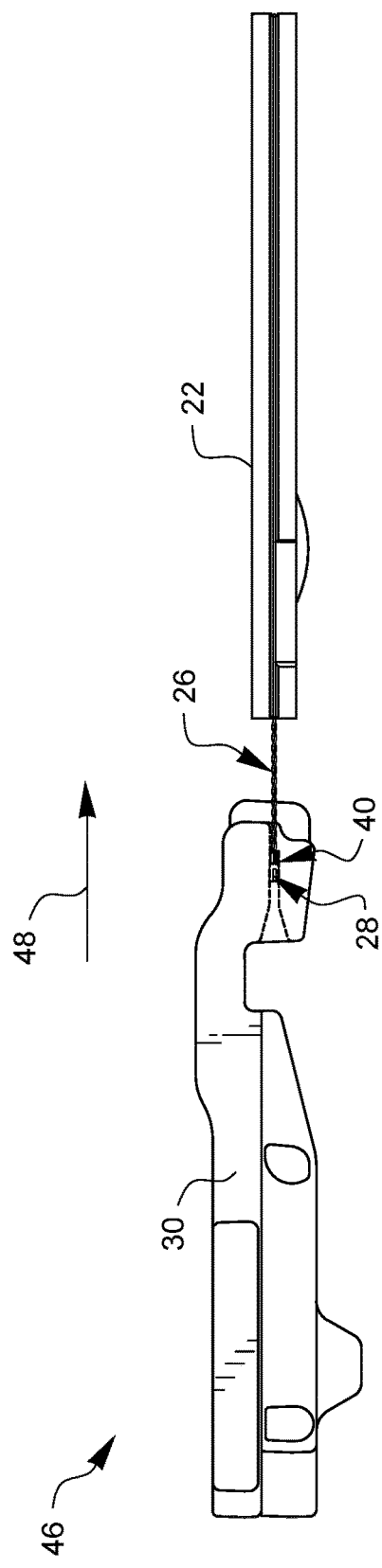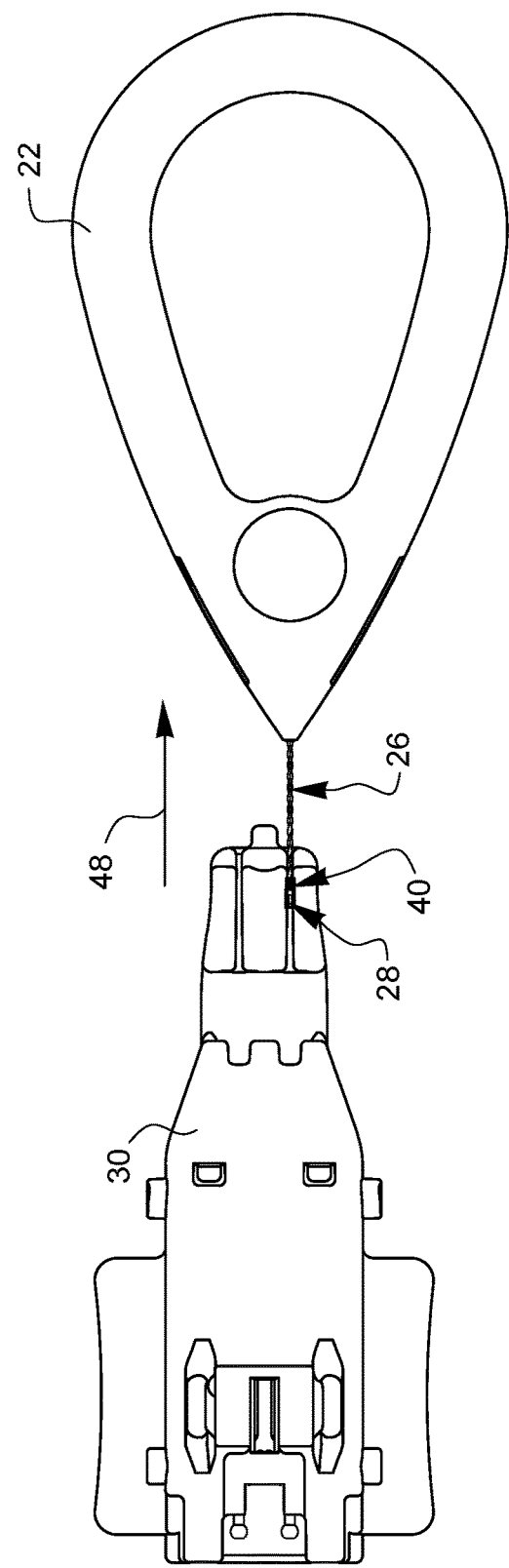
FIG. 4A
FIG. 4B

AUTOMATED SUTURING ADAPTER, ASSEMBLY, AND METHODS THEREOF

RELATED APPLICATION

This application claims priority to U.S. provisional patent application No. 62/607,811 filed Dec. 19, 2017 and entitled, "AUTOMATED SUTURING ADAPTER, ASSEMBLY, AND METHODS THEREOF". The 62/607,811 application is hereby incorporated by reference in its entirety.

FIELD

The claimed invention relates to surgical suturing devices, and more specifically to surgical suturing devices suitable for use with prosthetic devices, especially cardiac prosthetic devices such as replacement heart valves.

SUMMARY

An automated suturing adapter is disclosed. The automated suturing adapter has a target and a snare loop supported by the target. The automated suturing adapter also has a ferrule and a snare extension between the snare loop and the ferrule.

An assembly is also disclosed. The assembly includes a cassette. The cassette has a housing defining a suturing gap. The cassette also has a needle stored in the housing proximal to the suturing gap. The cassette further has a ferrule holder distal to the suturing gap. The assembly also includes a target and a snare loop supported by the target. The assembly further includes a ferrule held in the ferrule holder and a snare extension between the snare loop and the ferrule.

A method of suturing is further disclosed. A needle is actuated through a prosthetic sewing cuff and into coupling contact with a ferrule. The needle is retracted back through the prosthetic sewing cuff so that the ferrule and at least a portion of a snare extension coupled to the ferrule are also pulled back through the prosthetic sewing cuff. A suture end is passed through a snare loop coupled to an end of the snare extension opposite the ferrule coupled to the snare extension. The suture end is pulled through the prosthetic sewing cuff with the snare loop.

BACKGROUND

Modern advances in cardiac surgery have made it possible to replace heart valves using minimally invasive surgical techniques. As minimally invasive techniques have improved, surgeons are able to operate on patients through smaller and smaller access holes, resulting in less perioperative pain and shorter recovery times. A main focus of innovations in minimally invasive cardiac surgery has been on the tools which pass into the patient, through the small access holes, to place suture stitches more efficiently and reliably in tissue. By focusing on improvements to these steps of the surgical procedures, patients are able to be on cardio-pulmonary bypass machines for shorter times, thereby improving patient outcomes. Resultant efficiency improvements while working within the patient further help to reduce stress and fatigue on surgeons.

It would also be advantageous to focus on efficiency outside of the patient. Surgical teams are regularly working to streamline their own processes to enable surgeons to be as efficient as possible. In many minimally invasive surgical procedures, the ends of sutures which have been stitched within a patient are brought back out of the patient through one of the access sites so that the suture ends can be kept organized and then stitched through a sewing ring of a prosthetic device. Unfortunately, the suture ends often have connectors which were previously used to enable a corresponding minimally invasive suturing device to manipulate the suture ends within the patient. While it might be possible to reset these connectors (and therefore the suture ends) into the minimally invasive tissue suturing device, such devices are often not compatible with suturing a sewing cuff of a prosthetic device. As a result, surgical teams may be forced to cut off the connectors and thread each suture onto a needle in order to manually stitch each suture end through a prosthetic valve's sewing cuff. For many cardiac surgical procedures, unfortunately, this can increase the overall time a patient is on cardio-pulmonary bypass (CPB). Longer CPB times are associated with complications of the inflammatory system, heart, lungs, kidneys, and brain. Fortunately, devices have been developed which are compatible with specialized suture end connectors used by automated minimally invasive suturing devices to be transferred to a secondary automated suturing device for placing stitches efficiently and reliably through a prosthetic cuff. For example, the SEW-EASY® Device and Cassette System from LSI SOLUTIONS® (www.lsisolutions.com, Victor, N.Y.) is able to receive suture ends from their RAM® suturing device after it has been used to make an annular suture stitch in an aortic root anulus. The SEW-EASY® System may then be used to make a corresponding stitch to place the suture ends through a sewing cuff of a prosthetic valve. Such a system is indeed efficient and may enable surgical teams to complete cardiac surgical procedures more quickly for the benefit of the patient.

Benefits from using automated suturing devices for prosthetic sewing cuffs are often dependent on the prosthetic suturing device being compatible with a separate automated suturing device meant for use with tissue. Some surgeons, however, may prefer to use shafted instruments or other manual techniques to place stitches in tissue, especially in the field of cardiac surgery. Adoption of automated tissue suturing devices continues to grow and is certainly enabling for minimally invasive surgery, however, there will still be instances of preference for manual tissue suturing. It would be desirable, however, to be able to have an apparatus and method which would enable surgeons to use a suture with a needle to place annular sutures in a conventional, manual fashion while subsequently being able to use that suture with an automated suturing device for use in a prosthetic cuff, even if the needles on the ends of the suture are not compatible with the automated suturing system. It may be easier for surgeons to adopt automated suturing technology that is used outside of the patient (as is the case with prosthetic suturing devices), and such adoption may increase the rate of adoption for automated tissue suturing devices for use within a patient, thereby further enabling minimally invasive surgery.

BRIEF DESCRIPTION OF THE DRAWINGS

FIGS. 3A and 3B illustrate a snare extension of the automated suturing adapter of FIG. 1 inserted into a suture slot of the suturing cassette of FIGS. 2A, 2B in side and bottom views, respectively.

FIGS. 4A and 4B illustrate an embodiment of an automated suturing adapter assembly where a ferrule of the automated suturing adapter of FIG. 1 has been pulled into a ferrule holder of the suturing cassette of FIGS. 2A, 2B in side and bottom views, respectively.

Figure 1:
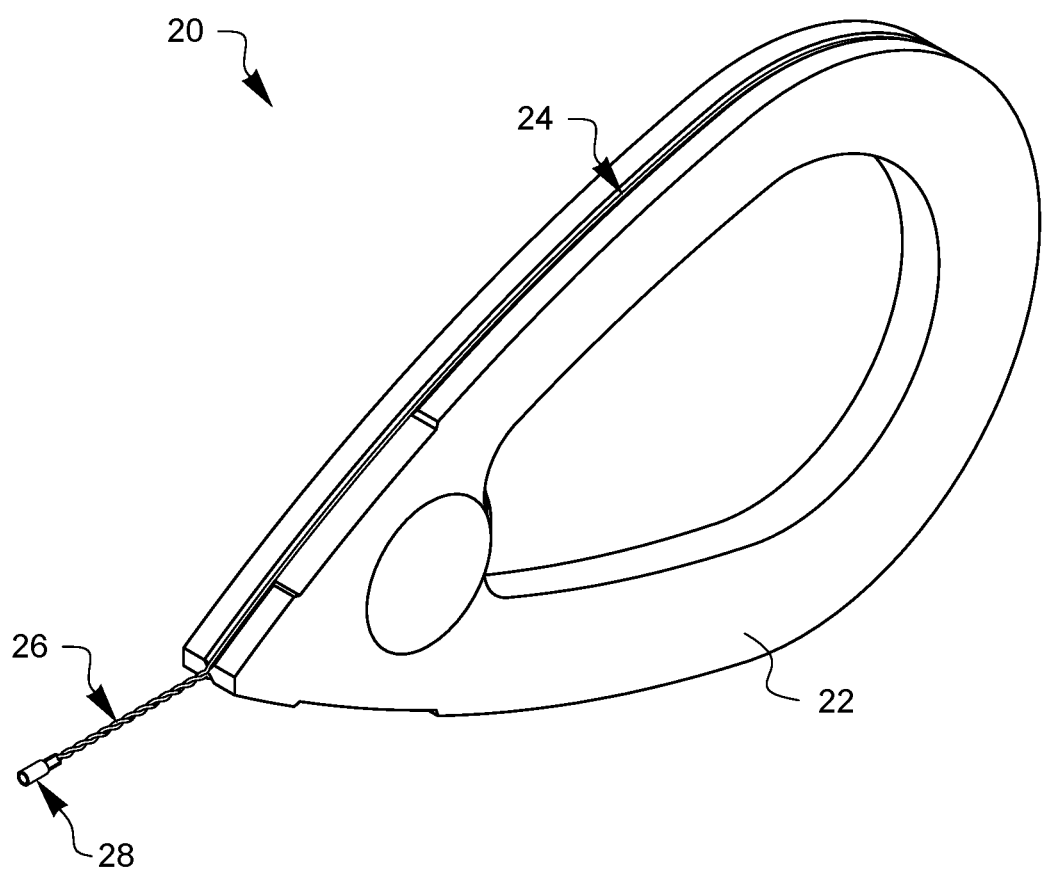
FIG. 1 is a perspective view of one embodiment of an automated suturing adapter.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 is a perspective view of one embodiment of an automated suturing adapter 20. The automated suturing adapter has a target 22 which supports a wire snare loop 24 (not completely visible in this view, but fully visible in FIGS. 5A and 5B). At least a portion of the target 22 is flexible to allow the target 22 to be removed from the snare loop 24. The target 22 may also, optionally be color-coded or marked in some way to indicate information about the suturing adapter 20, for example, with which automated suturing device or devices the suturing adapter 20 is compatible. A snare extension 26 extend away from the snare loop 24 and is coupled to a ferrule 28. In some embodiments, such as the one illustrated in FIG. 1, the snare extension 26 may be formed from twisted ends of the snare loop 24. In other embodiments, the snare extension 26 may be an untwisted extension. The snare loop 24 and the snare extension 26 may be formed from one or more of the following non-limiting materials: wire, metal, plastic, alloy, filament, suture, or any combination or plurality thereof.

The ferrule 28 may be sized to couple with a needle tip of an automated suturing device. The ferrule 28 may also be referred to as a needle cap, since it can resemble a cap placed over a needle tip when coupled with a needle. The suturing adapter 20 of FIG. 1 is intended to be used with automated suturing devices which utilize a needle and ferrule combination. One example of such an automated suturing device is the SEW-EASY® Device which works with the SEW-EASY® Cassette, both of which are sold by LSI Solutions, Inc. of Victor, N.Y. (www.lsisolutions.com). The SEW-EASY® Device has a lever which may be actuated to drive needles on a SEW-EASY® Cassette through a prosthetic sewing cuff and into contact with corresponding ferrules which are coupled to the ends of a suture. The ferrules stay attached to the needles and when the needles are withdrawn through the sewing cuff, the attached ferrules and the suture ends are also pulled back through the sewing cuff. In the rare, but possible, situation where a ferrule (and thus its suture) is not pulled back through the sewing cuff, a device such as the suturing adapter 20 of FIG. 1 may be helpful.

Figure 2A:
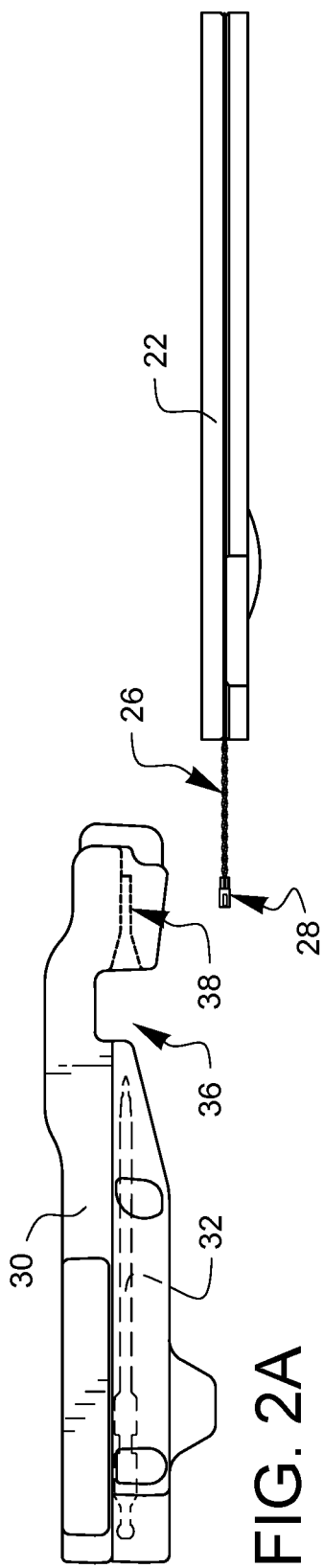
FIGS. 2A and 2B illustrate the automated suturing adapter of FIG. 1 and an embodiment of a suturing cassette for use in an automated suturing device in side and bottom views, respectively.
Figure 2B:
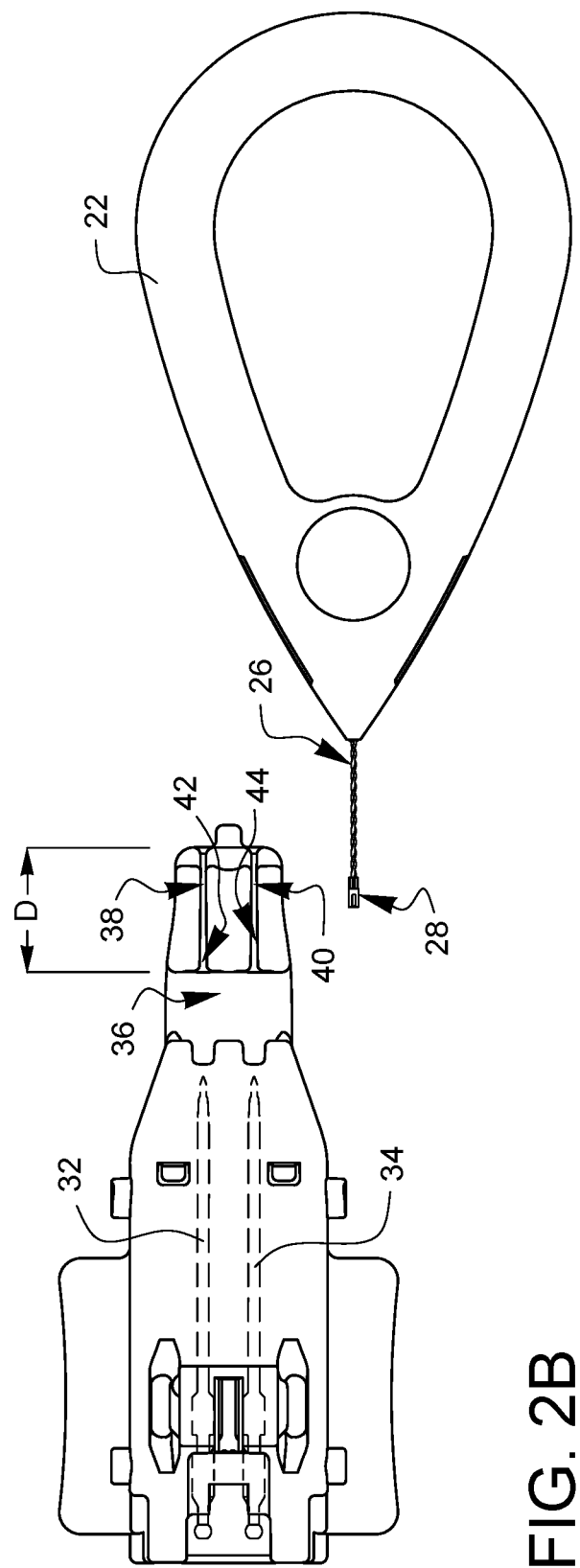

FIGS. 2A and 2B illustrate the automated suturing adapter of FIG. 1 and an embodiment of a suturing cassette 30 for use in an automated suturing device in side and bottom views, respectively. One example of a suitable suturing cassette 30 is the SEW-EASY® Cassette from LSI Solutions, Inc. discussed above. The suturing cassette 30 has two needles 32, 34 which may each be actuated by a SEW-EASY® Device as is known by those skilled in the art. When actuated, the needles 32, 34 cross a suturing gap 36 and move towards corresponding ferrule holders 38, 40. The cassette 30 also has suture slots 42, 44 which extend at least a distance D from the suturing gap 36 to a distal end of a corresponding ferrule holder 38, 40.

FIGS. 3A and 3B illustrate a snare extension 26 of the automated suturing adapter 20 of FIG. 1 inserted into a suture slot 44 of the suturing cassette 30 of FIGS. 2A, 2B in side and bottom views, respectively. The snare extension 26, which extends between the ferrule 28 and the target 22 should be at least as long as the distance D discussed above. This allows the snare extension 26 to sit in the suture slot 44 while the ferrule 28 sits in the suturing gap 36. Although only partially assembled in FIGS. 3A and 3B, the combined cassette 30 and automated suturing adapter 20 may be referred to as an automated suturing adapter assembly 46.

FIGS. 4A and 4B illustrate a fully assembled automated suturing adapter assembly 46 where the ferrule 28 of the automated suturing adapter has been pulled 48 into the ferrule holder 40 of the suturing cassette 30 in side and bottom views, respectively. Such an assembly is ready for use with an automated suturing device such as the SEW-EASY® Device described above.

Figure 5A:
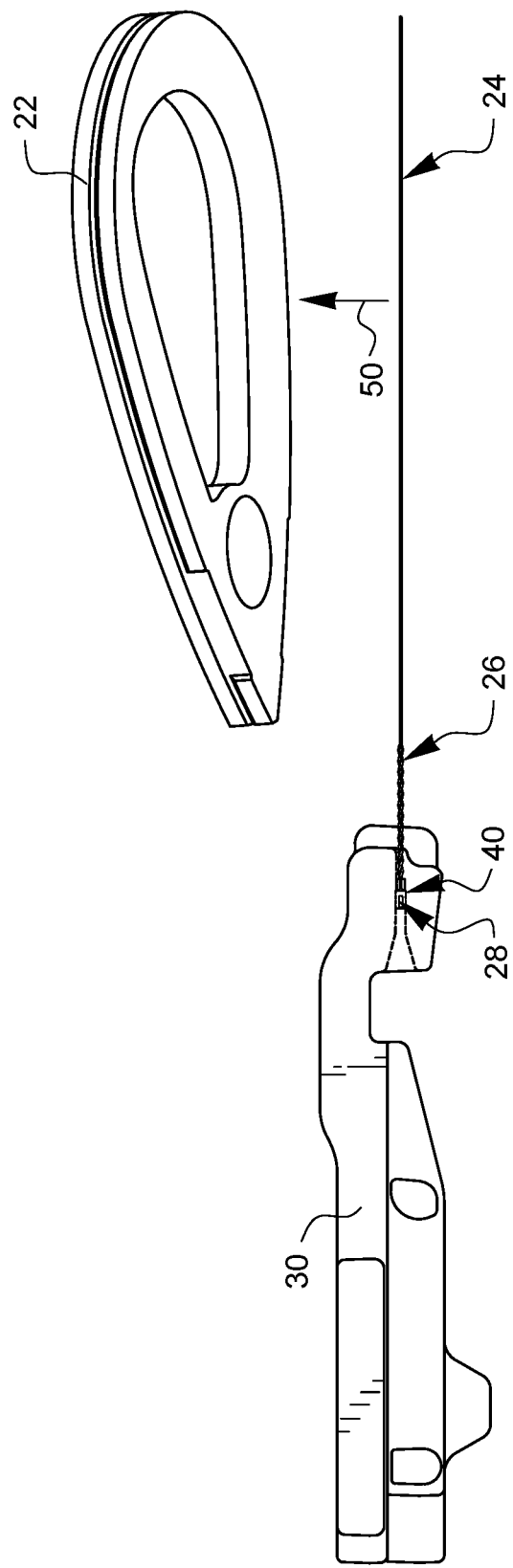
FIGS. 5A and 5B illustrate the automated suturing adapter assembly of FIGS. 4A, 4B with a target of the automated suturing adapter removed from the snare loop in side and bottom views, respectively.
Figure 5B:
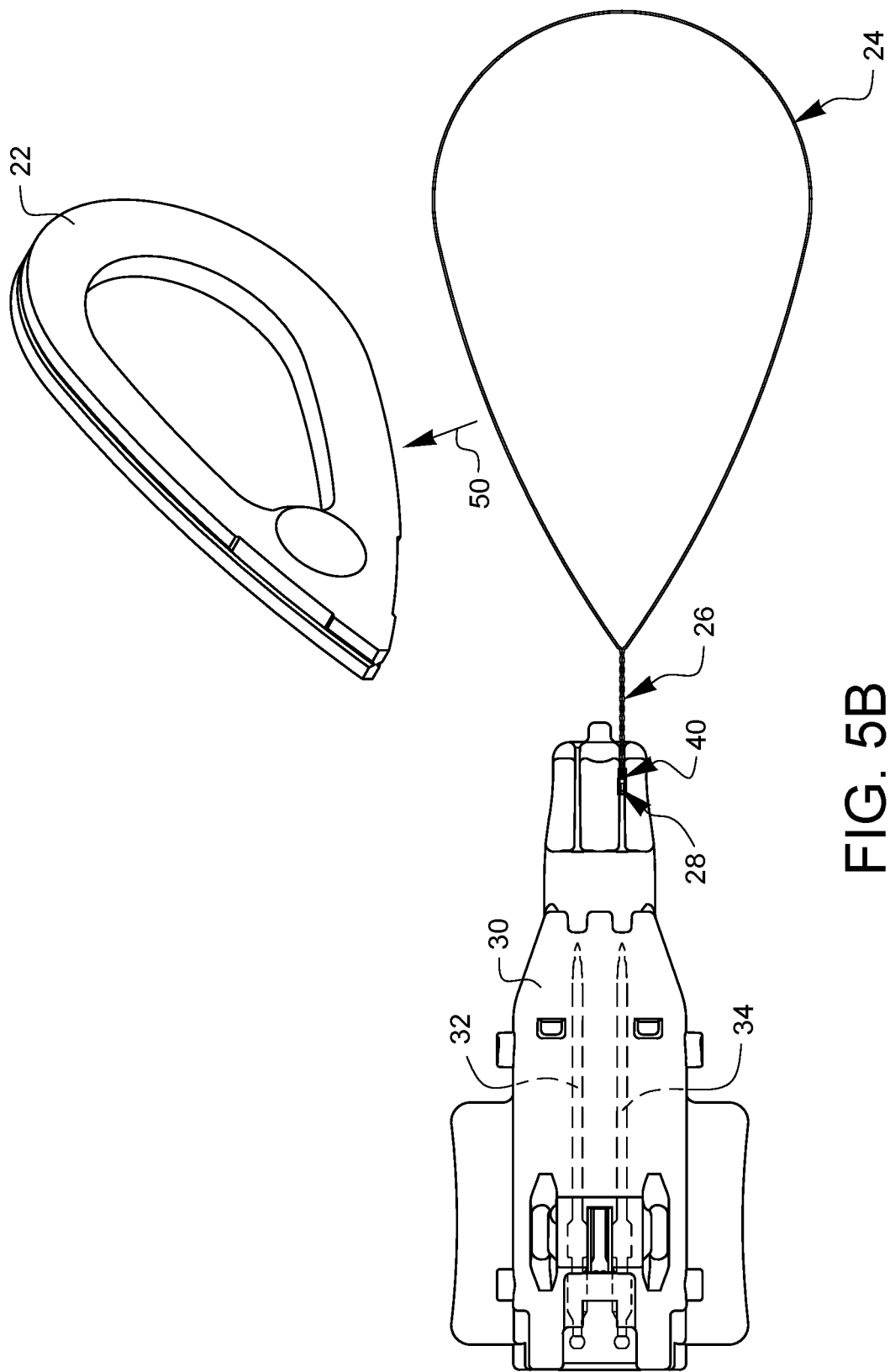

In order to utilize the automated suturing adapter assembly 46, the target 22 should be removed 50 from the snare loop 24 as illustrated in FIGS. 5A and 5B in side and bottom views, respectively. The target 22 could be removed 50 before or after the cassette 30 is loaded into the SEW-EASY® Device.

There are several non-limiting scenarios where the automated suturing adapter 20 or the automated suturing adapter assembly 46 could be useful. An automated suturing device such as the SEW-EASY® Device is used to place suture stitches through a sewing cuff of a prosthetic device. In normal use, a separate automated suturing device for tissue is used to stitch suture into tissue where the prosthetic device will eventually be installed. The ends of that suture are then installed in a SEW-EASY® Cassette, the cassette being installed in a SEW-EASY® Device. The prosthetic sewing cuff is placed into a suturing gap of the cassette and the needles are actuated through the sewing cuff and retracted to pick up the ferrules and its attached suture. Unfortunately, if the user does not have the suturing device aligned properly, it is possible for one of the needles to miss the cuff entirely. In this case, even though both ferrules may have been picked up properly, the ferrules are now coupled to the needles where they can't be retrieved and the cassette can't be reused. However, if the used cassette is cut from the suture ends, the automated suturing adapter 20 may be installed in a new cassette and used to pull the suture end through the sewing cuff in the manner described in the paragraph below. Similarly, even if the user has properly aligned both needles through the sewing cuff, there is a rare possibility that one of the ferrules does not get picked up by a needle. In this case, the used cassette may again be cut from the suture ends, and the automated suturing adapter 20 may be installed in a new cassette and used to pull the suture end through the sewing cuff in the manner described in the paragraph below. These two examples assume the user has used a compatible, ferrule-based device to place the suture stitches through tissue before trying to use a SEW-EASY® Device for automated suturing through a prosthetic cuff. If, however, a surgeon has manually placed stitches in tissue using suture with a needle, the surgeon may cut the needles off of the suture, and the automated suturing adapter 20 may be installed in a new cassette and used to pull the suture end through the sewing cuff in the manner described in the paragraph below.

Whether an automated suturing adapter 20 is installed in a new cassette to make an assembly or a ready-to-use automated suturing adapter assembly 46 is used, the cassette portion of the assembly is installed in an automated suturing device, such as the SEW-EASY® Device. The suturing gap 36 is aligned over the prosthetic sewing cuff so that the needle entrance and exit positions are as desired. The needles 32, 34 of the cassette 30 are advanced through the prosthetic sewing cuff and one of them 34 couples with the ferrule 28 of the automated suturing adapter. The needles 32, 34 are then retracted, pulling the ferrule 28 and the snare extension 26 through the prosthetic sewing cuff. The suture end (for example, from any of the examples in the preceding paragraph) is then placed into the snare loop 24, and the cassette 30 is used to pull the snare loop 24 and the suture end through the prosthetic sewing cuff. Depending on the starting scenario which led to the use of the automated suturing adapter, this allows recovery from a suture end which did not pick up properly the first time or which did not pass through the sewing cuff the first time. Alternatively, this enables an automated suturing device for prosthetics to be used with sutures placed manually through tissue.

Although the examples described above show the use of a single automated suturing adapter 20 with a cassette 30, in other embodiments, more than one automated suturing adapter 20 could be used with a cassette 30. In the example of the illustrated cassette 30, there are two suture slots 42, 44 and two corresponding ferrule holders 38, 40 which could be used to each hold a separate automated suturing adapter.

Figure 6:
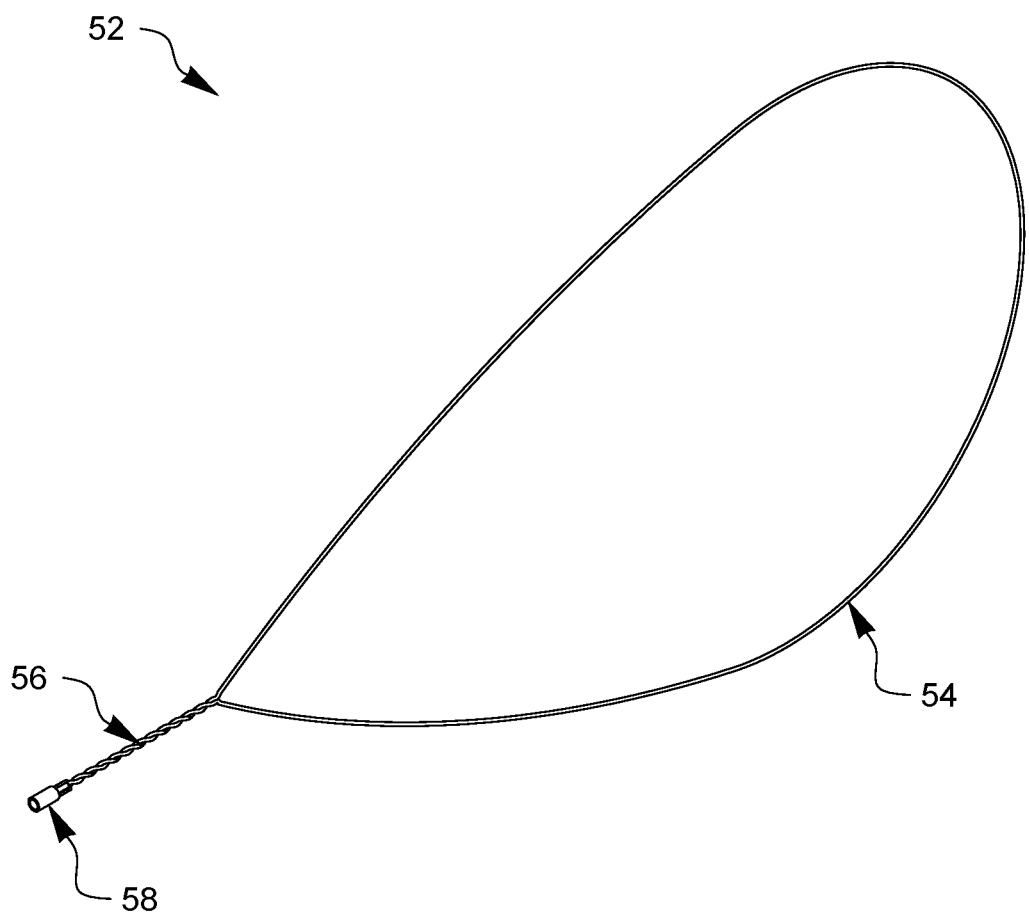
FIG. 6 is a perspective view of another embodiment of an automated suturing adapter.

FIG. 6 is a perspective view of another embodiment of an automated suturing adapter 52. This embodiment is similar to the embodiment of FIG. 1 but does not include a target. The target may be useful for helping to keep the snare loop open and to provide something which is more easily held and manipulated by a user, but it is not necessary in all contemplated embodiments. The automated suturing adapter 52 has a snare loop 54. A snare extension 56 extend away from the snare loop 54 and is coupled to a ferrule 58. In some embodiments, such as the one illustrated in FIG. 6, the snare extension 56 may be formed from twisted ends of the snare loop 54. In other embodiments, the snare extension 56 may be an untwisted extension. The snare loop 54 and the snare extension 56 may be formed from one or more of the following non-limiting materials: wire, metal, plastic, alloy, filament, suture, or any combination or plurality thereof.

Like the previous embodiments, the ferrule 58 may be sized to couple with a needle tip of an automated suturing device. The ferrule 58 may also be referred to as a needle cap, since it can resemble a cap placed over a needle tip when coupled with a needle. The suturing adapter 52 of FIG. 6 is intended to be used with automated suturing devices which utilize a needle and ferrule combination.

Various advantages of an automated suturing adapter, assembly, and methods thereof have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. An automated suturing adapter, comprising:
   a target;
   a snare loop supported by the target;
   a ferrule;
   a snare extension having a first end and a spaced apart second end, the first end coupled to the snare loop, the spaced apart second end coupled to the ferrule; and
   a cassette comprising a housing defining a gap, a proximal portion of the housing adjacent the gap is operable to maintain a first needle and a second needle adjacent the gap, a distal portion of the housing disposed adjacent the gap and spaced from the proximal portion, the distal portion comprising a first slot and a second slot, the first slot and the second slot extending from the gap to a terminal edge of the distal portion of the housing, the first slot and the second slot operable to hold the ferrule and the snare extension, the first slot located relative to the first needle such that movement of the first needle toward the gap allows the first needle to engage the ferrule disposed in the first slot when the ferrule engages with the first slot, the second slot located relative to the second needle such that movement of the second needle toward the gap allows the second needle to engage the ferrule disposed in the second slot when the ferrule engages with the second slot.

2. The automated suturing adapter of claim 1, wherein the target is at least partially flexible.

3. The automated suturing adapter of claim 1, wherein the snare extension comprises twisted wires.

4. An assembly, comprising:
   a cassette having:
      a housing defining a suturing gap;
      a needle stored in the housing proximal to the suturing gap; and
      a ferrule holder distal to the suturing gap, the ferrule holder defining a slot extending from the suturing gap to a terminal edge of the housing spaced from the needle;
   a target;
   a snare loop supported by the target;
   a ferrule; and
   a snare extension between the snare loop and the ferrule, wherein the slot is operable to hold the ferrule and a portion of the snare extension such that the snare loop is spaced from the housing proximal to the suturing gap, wherein the slot is located relative to the needle such that movement of the needle toward the suturing gap allows the needle to engage the ferrule disposed in the slot.

* * * * *